(12) United States Patent
Arad

(10) Patent No.: US 8,647,635 B2
(45) Date of Patent: Feb. 11, 2014

(54) COMPOSITIONS COMPRISING RED MICROALGAE POLYSACCHARIDES AND METALS

(75) Inventor: Shosh Arad, Omer (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 175 days.

(21) Appl. No.: 12/993,852

(22) PCT Filed: May 21, 2009

(86) PCT No.: PCT/IL2009/000505
§ 371 (c)(1),
(2), (4) Date: Nov. 22, 2010

(87) PCT Pub. No.: WO2009/144711
PCT Pub. Date: Dec. 3, 2009

(65) Prior Publication Data
US 2011/0070159 A1 Mar. 24, 2011

(30) Foreign Application Priority Data
May 26, 2008 (IL) .......................................... 191709

(51) Int. Cl.
*A61K 36/04* (2006.01)
(52) U.S. Cl.
USPC .................................................... 424/195.17
(58) Field of Classification Search
None
See application file for complete search history.

(56) References Cited

U.S. PATENT DOCUMENTS

| | | | | |
|---|---|---|---|---|
| 4,087,936 | A | * | 5/1978 | Savins et al. ............... 47/1.4 |
| 4,417,415 | A | | 11/1983 | Cysewski et al. |
| 4,746,504 | A | | 5/1988 | Nimrod |
| 4,824,673 | A | | 4/1989 | Herve et al. |
| 6,458,774 | B1 | | 10/2002 | Burger |
| 2007/0191303 | A1 | * | 8/2007 | Dillon et al. .................. 514/54 |
| 2009/0274736 | A1 | * | 11/2009 | Dillon et al. .................. 424/422 |

FOREIGN PATENT DOCUMENTS

| | | | |
|---|---|---|---|
| CN | 1563375 | * | 1/2005 |
| EP | 833645 | | 4/1998 |
| EP | 1536845 | | 6/2005 |
| WO | WO 97/00689 | * | 1/1997 |
| WO | 03/093322 | | 11/2003 |

OTHER PUBLICATIONS

Toncheva-Panova et al. Gen. Appl. Plant Physiology, Special Issue. 2006. vol. 32, pp. 53-60.*
Rahaoui et al. Mededelingen—Facuteit Landbouwkundige en Toegepaste Biologische Wetenschappen. 1998. vol. 63 (4b), pp. 1707-1710. CAPLUS Abstract enclosed.*
Ramus et al. J. Phycology. 1977. vol. 13, No. 4, pp. 345-348. Biosis Abstract enclosed.*
Damonte E B et al: "Sulfated seaweed polysaccharides as antiviral agents" Current Medicinal Chemistry 200409 NL, vol. 11, No. 18, Sep. 2004, pp. 2399-2419, XP002547219.
Pulz O el al: "Microalgae as source . . . polysaccharides", Progress in Plant Polymeric Carbohydrate Research, Jul. 3, 1992, p. 137/138, XP009021371.
Geresh Shimona et al: Chemically crosslinked polysaccharide . . . ions, Journal of Carbohydrate Chemistry, NY, US, vol. 16, No. 4-5, Jan. 1, 1997, pp. 703-708, XP009123125.
Schmitt D et al: "The adsorption kinetics . . . earth", Water Rsearch, Elsevier, Amsterdam, NL, vol. 35, No. 3, Feb. 1, 2001, pp. 779-785, XP004321652.
Rahaoui A et al: "Uptake of three toxic..violacea", Mededelingen Van De Faculteit Landbouwwetenschappen Univ., Gent, BE, vol. 63, No. 4b, Jan. 1, 1998, pp. 1707-1710, XP009123126.
Toncheva-Panova, Tonka et al: "Preparation of nanonnatrix.. algal cells" Dokladi Na Bolgarskata Akademiya Na Naukite, vol. 61, No. 2, 2008, pp. 211-216, XP009123234.
Palamaru Ilana et al: "Bioaccumulation of radioactive zinc-65 ions", Revue Roumaine de Biochemie, vol. 33, No. 3-4, Jul. 1996, pp. 215-219, XP009123237.
IPRP for corresponding PCT application (7 pages) mailed Nov. 30, 2010.

* cited by examiner

*Primary Examiner* — Chris R Tate
(74) *Attorney, Agent, or Firm* — Roach Brown McCarthy & Gruber, P.C.; Kevin D. McCarthy

(57) ABSTRACT

Provided is a composition which contains a red microalga polysaccharide and a heavy metal, which is used as a cosmetic, diagnostic, or pharmaceutical formulation. The pharmaceutical formulation may be employed topically or for treating nutritional and other disorders.

7 Claims, No Drawings

US 8,647,635 B2

COMPOSITIONS COMPRISING RED MICROALGAE POLYSACCHARIDES AND METALS

REFERENCE TO CO-PENDING APPLICATIONS

Priority is claimed as a 371 of international application number PCT/IL2009/000505, filed on May 21, 2009, which claims priority to Israeli patent application serial number 191709, filed on May 26, 2008.

FIELD OF THE INVENTION

The present invention relates to complexes of red microalgae polysaccharides with metals, to pharmaceutical cosmetic and nutritional compositions comprising them, and to their applications.

BACKGROUND OF THE INVENTION

Metals are used in diverse pharmaceutical compositions for treating metal deficiencies and other metal-associated conditions. Metal deficiencies may result in various disorders, including cardiovascular diseases, diabetes, high blood pressure, hair loss, skin lesions, impaired cognitive and motor functions; nutritional additives may be tried to compensate for the deficiency. However, the form of metal delivery in treating said deficiencies or other metal-responding conditions is critical, in view of problems with metal availability and toxicity. Attempting to provide a suitable metal delivery means, hyaluronic acid has been employed for complexing metals to be delivered. U.S. Pat. No. 4,746,504 relates to metal salts of hyaluronic acid and their use as antimicrobial agents. U.S. Pat. No. 6,458,774 relates to hyaluronic acid complexes with metals, and to pharmaceutical compositions containing them. Hyaluronic acid, a fundamental component of the connective tissues, is easily biodegradable and does not show too a high residence time in a usual biological environment. Other polysaccharides have been tried for use in metal binding, such as oxidized cellulose, which was disclosed in EP 1536845 as a wound dressing in complex with silver.

It is an object of the invention to provide a metal delivery and supply means based on polysaccharides.

It is further an object of the invention to provide a metal/polysaccharide composition for treating metal associated conditions.

It is a still further object of the invention to provide a pharmaceutical or cosmetic composition comprising a metal/polysaccharide complex for treating skin conditions.

Other objects and advantages of the present invention will appear as the description proceeds.

SUMMARY OF THE INVENTION

The invention provides a composition comprising a red microalgae polysaccharides (RMP) and a metal. In a preferred embodiment of the invention, said metal is at least partially bound in a metal/polysaccharide complex comprising the glucuronic acid residues and/or sulfated monosaccharide residues of a red microalga polysaccharide. Said red microalga may belong to genus *Porphyridium*. Said composition may have a consistency of solution, nanoparticle suspension, or gel. In an important aspect of the invention, said RMP/metal composition is a pharmaceutical formulation, comprising at least one RMP, at least one metal, and component selected from diluents, excipients, carriers, stabilizers, surfactants, and odorants. The formulation may further comprise a second pharmaceutically active agent selected from antiviral, antifungal, antibacterial, antiseptic, anti-inflammatory or immunomodulatory, antineoplastic, analgesic, and drugs for treating burn wounds. In another important aspect of the invention, the composition is a cosmetic composition, comprising at least one RMP, at least one metal, and a component selected from diluents, carriers, stabilizers, surfactants, and odorants. Said cosmetic composition may be a gel, lotion, cream, or may have other known form. Said metal is preferably selected from the $4^{th}$ and $5^{th}$ period of the element table. In preferred embodiments, said metal is selected from the group consisting of zinc (Zn), copper (Cu), selenium (Se), nickel (Ni), and silver (Ag). In another aspect of the invention, said composition may be a diagnostic or imaging or contrast composition. The composition of the invention may comprise a radioactive isotope. Preferably, the metal constitutes from 0.0001 wt % to 4 wt % of said RMP/metal complex.

The invention is directed to the use of an RMP/metal compositions in treating a condition selected from nutritional disorders, gastrointestinal disorders, dermatologic disorders, proliferative disorders, immunologic disorders, and infectious diseases.

A composition according to the invention may act as an antioxidant, anti-irritant agent, antimicrobial agent, or anti-inflammatory agent, preferably applied topically.

The invention is directed to a process for preparing a composition comprising RMP and a metal, comprising the steps of: i) providing a solution of at least one RMP in a water-based solvent; ii) contacting said RMP solution with a metal compound, thereby obtaining a mixture with at least a part of said metal being bound in an RMP/metal complex; iii) optionally sterilizing said mixture; and optionally; iv) removing at least a part of said solution from said mixture; thereby obtaining a homogeneous composition comprising intimately mixed polysaccharide and metal. Said sterilization may be effected by any known means, comprising thermal means, chemical means, physical means, etc. Said thermal means may comprise autoclaving, said physical means filtration. A skilled person will choose a suitable means; for example, zinc complexes may be autoclaved, silver complexes filtered, etc. Of course, the pH value will be carefully controlled, as mentioned below. Said solution of at least one RMP may comprise an alga cultivation medium. In one embodiment of said process of the invention, said metal compound is added into the growth medium of said microalga, followed by extracting from the cells a fraction enriched with metal/RMP complex. Said metal compound is preferably a water-soluble metal salt. In a preferred process for making said composition, the following steps are involved: i) cultivating a red alga of genus *Porphyridium*; ii) isolating a RMP from the cultivating mixture; Hi) contacting, in an aqueous reaction mixture, said RMP with a metal compound containing an amount of said metal of from 0.0001 wt % to 4 wt % in regard to the total weight of the RMP and the metal; and iv) mixing said aqueous reaction mixture for at least 30 minutes at ambient temperature. Said metal is in some of preferred embodiments selected from Zn, Cu, Se, Ni, and Ag. In other embodiments, said alga may comprise other genera, such as, for example, *Rhodella* and *Dixoniella*; examples of species that can be employed include various *Porphyridium* sp., *Rhodella reticulate* (*Dixoniella grisea*), etc.

The invention relates to the use of a RMP/metal complex in the preparation of a medicament. Also provided is a method of treating a subject suffering from a condition selected from nutritional disorders, gastrointestinal disorders, dermatologic disorders, proliferative disorders, immunologic disorders, and infectious diseases, comprising administering to said subject a RMP/metal complex. The invention provides functional food or medicinal food containing red microalgae polysaccharides (RMP) with a health-enhancing metal, for slow release of said metal; a preferred example of the metal is Zn.

DETAILED DESCRIPTION OF THE INVENTION

It has been found that a surprisingly efficient metal delivery composition is obtained when combining a microalga polysaccharide with a metal such as Zn or Cu in an amount of 1-2 wt %, based on the polysaccharide mass. However, other metals are advantageously combined with red algae polysaccharides, in various ratios, the polysaccharides being selected, for example from polysaccharides produced by *Porphyridium, Rhodella*, or *Dixoniella*, and the metals being selected preferably from the $4^{th}$ and $5^{th}$ period of the element system.

The present invention relates, in one aspect to complexes of red microalgae polysaccharides and metals, and to pharmaceutical, cosmetic, and nutritional compositions comprising them. In another aspect, the invention relates to a composition comprising a red microalga polysaccharide (RMP) and a metal, wherein the metals are either chemically bonded to the anionic groups of said polysaccharides, or they are homogeneously admixed in the composition with the polysaccharides, for example as nanoparticles. Said bond may comprise ionic interactions or for example coordination complexing. Said metal preferably constitutes from 0.0001 to 4 wt % of the total RMP/metal weight.

The present invention relates to the use of said compositions for treating various conditions, including infectious diseases, cancer, and burns. The complexes of the invention may comprise, for example, Zn, Ag, Cu, Se, or mixtures thereof, wherein the treatment, in one aspect, is topical. In another aspect, the complexes are a source of therapeutic metal to be slowly released in the body in a specific organ. The term metal is intended to include a metal having the mass number of at least 44, including stable or radioactive isotopes.

Certain conditions, such as acne, rash, skin irritation and dandruff affect the skin and joints, their symptoms varying from red rash to open ulcers and arthritis. The chronic form of these diseases may be associated with infections, and the treatments that have been proven effective include topical application of oxidizers, antibacterial or antiviral products, and oral administration of antibiotics. Antiviral and antibacterial agents are often unavailable or ineffective, and they cause side-effects, while their repeated use contributes to the appearance of resistant strains; the oxydizers, on the other hand, may easily cause damages to the skin. Beneficially, the treatment with metal ions is broadly effective in preventing and treating all sorts of infections, greatly reducing the risk of the emergence of a new resistant strain. Examples of metal treatments include the use of zinc sulfate in controlling joint problems caused by arthritis in psoriasis patients. Copper-based compounds have been used to treat rheumatoid arthritis and to affect inflammation in the joints. Gold compounds were once the only agents available in treating arthritis. Silver has been used as an antibacterial agent for topical use. In a preferred embodiment, Ag-complexes are applied in treating burns. Pharmaceutical preparations containing the above specified metals and others, are well known and are commonly used for treating burns, wounds and skin infections. In addition, zinc, copper, silver and other metal ions have all been shown to interfere with various bacterial metabolic pathways. However, metals must be very carefully dosed, their therapeutic range being often dangerously narrow. Therefore, the way of metal administration and transport is extremely important. In order to improve the stability and bioavailability of the metal ions, polysaccharide-metal complexes, particularly complexes of hyaluronic acid and its derivatives with metals, were suggested, as mentioned above.

The instant invention employs red microalgae, and thus brings distinct advantages over hyaluronic acid. Firstly, red microalgae polysaccharides are not degraded so easily in mammalian tissues, while exhibiting low antigenicity. Secondly, red microalgae polysaccharides comprise among their monosaccharide building blocks additional monosaccharides that contribute to efficient metal binding. Generally, the RMP are resistant toward hyluronidase and various carbohydrolases, as well as toward pH changes, heating and higher temperatures. There is not one single type of metal binding within the red microalgae chains, and the attachment mechanisms are not a part of the invention, but it seems that the presence of the sulfated groups beside glucuronic acid, and the concentration ratios between various metal-binding chemical groups constitute an optimal configuration for attaching metals and their gradual release. Of course, various binding mechanisms may participate. The invention thus relates to a controlled release of metals in treating metal-responding conditions. A skilled person will realize that algal polysaccharides may play a role of an ion exchanger, wherein hydrogen or alkali metal cations in the carboxyl or sulfate groups may be replaced with metal atoms. Binding metals in complexes, for example as cations complementing anionic RMP groups, enables storage and gradual release of metallic components. Known effects of the pH on creating metal complexes and on their properties, such as solubility and other, will of course be taken into consideration by a skilled person when contacting the RMP with metals. Also a part of the invention is an homogeneous composite phase comprising RMP/metal, where said metal may be finely interspersed with the polysaccharide, forming nanoparticles in an intimate contact with polysaccharide chains. The RMP have good adsorbing properties, which is particularly advantageous in skin treatments.

The treatment of various conditions, by providing compositions with sustained release of metal atoms or ions, include the antimicrobial action of silver complexes, antioxidative action of selenium complexes, and dermatologic action of zinc complexes.

Some previously used polysaccharides are not sufficiently stable and degrade too quickly, while others induce irritation or immune responses, and still others show unsuitable structure changes when reacting with metal ions. However, polysaccharides from red microalgae, such as for example species belonging to *Porphyridium* genus, are surprisingly well suited for pharmaceutical metal delivery: they lack the above named drawbacks of many other polysaccharides; moreover, said polysaccharides can be easily produced in large quantities. Beside being stable and biocompatible, said polysaccharides posses antimicrobial properties and antiviral properties (EP 833 645).

Red microalgae cells grow rapidly under controlled conditions and are naturally encapsulated by sulfated polysaccharides, whose molecular mass may go up to 3-5 million daltons. The polysaccharides can be harvested in several methods for different uses. The produced polysaccharides are stable in solution even when exposed to a wide range of pH values and temperatures. They are not only indigestible by the enzymes present in the mammalian gastrointestinal tract, but they are not cleaved by most of commercially available carbohydrolases.

Advantageous properties of the red algae polysaccharides have now been combined with therapeutic action of metals. Controlled metal release is ensured by the instant compositions; superior properties are achieved in comparison with other metal-releasing therapeutic agents. Compositions comprising said combined polysaccharides and metals are capable of inhibiting the proliferation of cancer cells, and preventing or treating many infectious diseases.

In one aspect, a silver complex with *Porphyridium* sp. polysaccharide inhibited nearly completely the growth of *E. coli*, when the amount of said complex corresponded to 10 ppm-50 ppm Ag.

Provided by the invention is a method of manufacturing a pharmaceutical composition, comprising providing a red alga polysaccharide dissolved in an aqueous solvent, contacting said solution with a metal in an amount of up to 4 wt % based on said polysaccharide, and optionally removing at least a part of said solvent, thereby obtaining a composite phase to be used directly or after formulating. Said composite phase may comprise metal chemically bonded to the polysaccharide, metal finely dispersed in a hydrophilic matrix, solution, gel, or a combination thereof. In one embodiment, said manufacturing method comprises steps of a) treating a polysaccharide (PP) aqueous solution with a cation exchanger to remove metal ions, and b) adding a salt of the required metal in an aqueous solution, such as for example $AgNO_3$ or $ZnCl_2$, to a PP solution rid of other metals from step a), and c) dialyzing against water or buffer. Said step b) may comprise mixing for about 30 minutes. Said step c) removes an excess of said required metal in the mixture. Said step of contacting may follow or precede the step of isolation the red microalga polysaccharide from cultivation medium, or may be a part of the growth process or during the cross flow filtration.

In an example of a composition according to the invention, an algal polysaccharide in complex with silver was prepared, and stored for 8 weeks in physiological solution, in dark at the temperature of 4° C., without detecting any degradation as indicated by viscosity.

This invention provides a composition containing a red microalgal polysaccharide and a metal for use in therapy, more specifically, in topical therapy. A composition according to the invention may have a consistency of solution, suspension, or gel.

The invention relates to a composition comprising a complex of a metal with at least one RMP. Further, the invention relates to a pharmaceutical or cosmetic formulation comprising red microalga polysaccharide complex with a metal, further possibly comprising excipients, carriers, stabilizers, adjuvants, diluents, surfactants, odorants, and a second pharmaceutically active agent selected from antiviral, antifungal, antibacterial, antiseptic, anti-inflammatory or immunomodulatory, antineoplastic, and analgesic. The formulation may be a topical composition for preventing, ameliorating, and healing a skin or mucosa condition comprising viral infection, microbial infection, acne, dermatitis, or burns, wherein all components are acceptable for topical use. The topical formulation may be used for enhancing wound closing. A composition according to the invention is preferably a homogeneous mixture having a consistency of cream, lotion, ointment, pomade, or gel. In one embodiment, the composition comprising a complex of red microalga polysaccharide with a metal is formulated for parenteral use, either as a therapeutic agent or as a diagnostic agent.

In a preferred embodiment of the invention, said metal is zinc. The invention provides a pharmaceutical formulation comprising an RMP and zinc. The zinc amount may be in the range of from 0.02 to about 2 wt % based on the RMP weight.

The invention also provides a cosmetic formulation comprising an RMP and zinc. In a preferred embodiment, a topical formulation comprising a zinc/RMP complex is provided for treating dermatological conditions, particularly acne and dermatitis. In another preferred embodiment, food or a food additive comprising a zinc/RMP complex is provided as a health enhancer in cases when zinc is indicated, an example being nail growth.

In other preferred embodiment of the invention, said metal is copper. The invention provides a pharmaceutical formulation comprising an RMP and copper. The cooper amount may be from 0.02 to 2 wt % based on the RPM weight. In a preferred embodiment, a topical formulation comprising a copper/RMP complex is provided for treating inflammation, and for stimulating immune system.

In another preferred embodiment of the invention, said metal is selenium The invention provides a pharmaceutical formulation comprising an RMP and selenium. In a preferred embodiment, a topical formulation comprising a selenium/RMP complex is provided for treating selenium-responding conditions. In another preferred embodiment, a formulation comprising a selenium/RMP complex is provided for cosmetic treatment of skin conditions responding to selenium. In other preferred embodiment, food or food additive comprising a selenium/RMP complex is provided for enhancing health in subjects with selenium deficiency or subjects positively reacting to increased selenium intake, or in cases when selenium as an antioxidant is indicated.

In a still another preferred embodiment of the invention, said metal is silver. The invention provides a pharmaceutical formulation comprising an RMP and silver. In a preferred embodiment, a formulation comprising a silver/RMP complex is provided for treating infections or conditions aggravated by infections or associated with infection, particularly bacterial infections. An important embodiment of the invention is the use of silver/RMP-comprising compositions in treating burns.

The invention provides compositions comprising RMP/metal complex. Said composition is in one embodiment an antimicrobial composition, an antiinflammatory composition, or an antioxidative composition. It may be used as a topical formulation, either pharmaceutical or cosmetic. In other embodiment, a composition is provided which is cytotoxic, either for topical use or for parenteral administration. The composition may be used, for example, in an anti-proliferative treatment.

This invention also relates to the use of red algae polysaccharides and metal in the preparation of compositions for treating arthritis and other joint disorders, preferably osteoarthritis, rheumatoid arthritis, gout, arthritis, trauma and (age related) degeneration, wherein said composition is preferably a non-immunogenic, non-toxic, water solution.

It is a still further purpose of this invention to provide a method for preparing the red algae polysaccharide-metal complexes of the invention, and pharmaceutical compositions containing the same for topical, oral or internal administration. In a specific embodiment, the pharmaceutical compositions are used for preventing or treating cancer and infectious diseases.

Thus, the invention is directed to synergistically beneficial action of RMP and metals; the two components may be associated in many ways—embodiments, each of which has special advantages. In many applications, it will be advantageous to contact an essentially pure RMP with a metal salt; in certain modifications, metals may be added to the growth medium; however, other techniques may be utilized, comprising processing cell extract, enriched cell extract, etc. The RMP may be first processed and later reacted with a metal compound, wherein said RMP processing may comprise known preparative techniques, such as solvent precipitation, chromatography, various filtration techniques, dialysis, etc.

The invention will be further described and illustrated in the following examples.

EXAMPLES

Cultivation of Algae

Red microalgae of *Porphyridium* sp. was grown in an artificial sea water (ASW) medium under controlled conditions, and in a large-scale setup, as follows: A piece of slant was transferred aseptically to each sterile Erlenmeyer flask containing 100 ml of ASW. The Erlenmeyer flasks were maintained in a controlled growth room on shaker with light supplied from above by fluorescent lighting of about 90 mEm-2s-1 intensity, at a temperature of 25+3° C. After 7-10 days the volume of each Erlenmeyer flask was transferred to a polyethylene sleeve. Each sleeve was filled to a final volume of 3.0 liters of cultures were mixed with air containing 1-3% $CO_2$ at a flow rate of 2 liters per minute. The logarithmic phase of growth was followed by the stationary phase during which the polysaccharide accumulated in the growth medium. After 15-20 days, the polysaccharide was harvested from the enriched medium.

Isolation of the Red Algae Polysaccharide

The cells of the red microalgae are encapsulated within a sulfated polysaccharide, the external part of which dissolves in the medium. When the algae are grown in a liquid medium, the viscosity of the medium increases due to the dissolution of the polysaccharide from the cell surface. The cells were separated from the supernatant using a continuous centrifugation and the supernatant was collected. The polysaccharide was treated further by using cross flow filtration technology for removing salts to and concentrating the polysaccharide. The final product had >0.9%, viscosity >1400 cP.

The polysaccharide has been tested for toxicity (irritation of the eyes) and was found to be safe for use on animals.

While this invention has been described in terms of some specific examples, many modifications and variations are possible. It is therefore understood that within the scope of the appended claims, the invention may be realized otherwise than as specifically described.

The invention claimed is:

1. A process for preparing a solution comprising a red microalga polysaccharide and a heavy metal compound selected from Zn, Cu, Se, Ni, Mn, and Ag bound to glucuronic monosaccharide residues and/or sulfated monosaccharide residues of said polysaccharide, consisting of the steps of:
   i) cultivating a red microalga of the genus selected from *Porphyridium*, *Rhodella*, and *Dixoniella*, in a cultivation mixture, thereby obtaining red microalga polysaccharide (RMP) dissolved in said mixture;
   ii) separating the microalga cells from said cultivation mixture; and
   iii) contacting the RMP in said cultivation mixture, before or after separating said microalgae cells therefrom, at a pH of sea water, with the heavy metal compound at a concentration higher than needed for supplying micronutrients to said microalga, said heavy metal compound being in an amount of from 0.02 to 2 wt % based on the RMP weight, thereby obtaining said solution.

2. A process for preparing a solution comprising a red microalga polysaccharide and a heavy metal selected from Zn, Cu, Se, Ni, Mn, and Ag bound to glucuronic monosaccharide residues and/or sulfated monosaccharide residues of said polysaccharide, consisting of the steps of:
   i) cultivating a red microalga of the genus selected from *Porphyridium*, *Rhodella*, and *Dixoniella*, in a cultivation mixture, thereby obtaining red microalga polysaccharide (RMP) dissolved in said mixture;
   ii) separating the microalga cells from said cultivation mixture;
   iii) contacting the RMP in said cultivation mixture, before or after separating said cells from said mixture, at a pH of sea water, with the heavy metal compound at a concentration higher than needed for supplying micronutrients to said microalga, said heavy metal compound being in an amount of from 0.02 to 2 wt % based on the RMP weight, to obtain a RMP/heavy metal complex mixture; and
   iv) a step selected from the group consisting of sterilization, treating with an ion exchanger, dialyzing, or filtration of the mixture obtained in step iii), thereby forming said solution.

3. The process according to claim 2, wherein said step of filtration comprises cross flow filtration.

4. The process according to claim 3, wherein said cross flow filtration provides a solution containing RMP/heavy metal complex at a concentration greater than 0.9 wt %.

5. The process according to claim 3, wherein said cross flow filtration provides a solution containing RMP/heavy metal complex exhibiting viscosity greater than 1400 cP.

6. A process for preparing a solution comprising a red microalga polysaccharide and a heavy metal compound selected from Zn, Cu, Se, Ni, Mn, and Ag bound to glucuronic monosaccharide residues and/or sulfated monosaccharide residues of said polysaccharide, consisting of the steps of:
   i) cultivating a red microalga of the genus *Porphyridium* in a cultivation mixture, thereby obtaining red microalga polysaccharide (RMP) dissolved in said mixture;
   ii) isolating said RMP from said cultivating mixture;
   iii) contacting said RMP in an aqueous reaction mixture after its isolation from said cultivation mixture, at a pH of sea water, with said heavy metal compound at a concentration higher than needed for supplying micronutrients to said RMP, said heavy metal compound being in an amount of from 0.02 to 2 wt % based on the RMP weight; and
   iv) mixing said aqueous reaction mixture for at least 30 minutes at ambient temperature, thereby obtaining said solution.

7. A process for preparing a solution comprising a red microalga polysaccharide and a heavy metal compound selected from Zn, Cu, Se, Ni, Mn, and Ag bound to glucuronic monosaccharide residues and/or sulfated monosaccharide residues of said polysaccharide, consisting of the steps of:
   i) cultivating a red microalga of genus *Porphyridium* in a cultivation mixture, thereby obtaining red microalga polysaccharide (RMP) dissolved in said mixture;
   ii) adding said heavy metal compound to cultivation mixture at a concentration higher than needed for supplying micronutrients to said microalga, said heavy metal compound being added in an amount of from 0.02 to 2 wt % based on the RMP weight to said cultivation mixture, at a pH of sea water, before separating the microalga cells from said mixture;

iii) separating the microalga cells from said cultivation mixture, thereby obtaining said solution.

* * * * *